(12) United States Patent
Christmann et al.

(10) Patent No.: US 12,263,321 B2
(45) Date of Patent: Apr. 1, 2025

(54) METHOD FOR ASCERTAINING THE VERTICAL DISTANCE BETWEEN A PATIENT (LEVEL OF SURGICAL INTERVENTION) AND A FLUID DELIVERY PUMP

(71) Applicant: W.O.M. WORLD OF MEDICINE GMBH, Berlin (DE)

(72) Inventors: Thomas Christmann, Berlin (DE); Jan Hendrik Carstens, Berlin (DE); Hans-Joachim Cappius, Berlin (DE)

(73) Assignee: W.O.M. WORLD OF MEDICINE GMBH, Berlin (DE)

( * ) Notice: Subject to any disclaimer, the term of this patent is extended or adjusted under 35 U.S.C. 154(b) by 1025 days.

(21) Appl. No.: 17/052,299

(22) PCT Filed: May 2, 2019

(86) PCT No.: PCT/DE2019/000118
§ 371 (c)(1),
(2) Date: Nov. 2, 2020

(87) PCT Pub. No.: WO2019/210894
PCT Pub. Date: Nov. 7, 2019

(65) Prior Publication Data
US 2021/0236711 A1    Aug. 5, 2021

(30) Foreign Application Priority Data

May 2, 2018    (DE) ...................... 10 2018 003 519.1

(51) Int. Cl.
*A61M 3/02*    (2006.01)

(52) U.S. Cl.
CPC ........ *A61M 3/0216* (2014.02); *A61M 3/0258* (2013.01); *A61M 3/0202* (2021.05); *A61M 2205/3327* (2013.01); *A61M 2205/3344* (2013.01); *A61M 2205/6054* (2013.01); *A61M 2205/6072* (2013.01)

(58) Field of Classification Search
CPC .............. A61M 3/0216; A61M 3/0258; A61M 3/0202; A61M 2205/332; A61M 2205/3327; A61M 2205/3331; A61M 2205/3334; A61M 2205/3337; A61M 2205/3344; A61M 2205/3348; A61M 2205/3355; A61M 2205/3358; A61M 5/168; A61M 5/16818; A61M 2205/52; A61B 5/03; F04B 2205/01; F04B 2205/05
See application file for complete search history.

(56) References Cited

U.S. PATENT DOCUMENTS

| | | | |
|---|---|---|---|
| 4,795,424 A | 1/1989 | Burner | |
| 6,503,062 B1 * | 1/2003 | Gray | A61M 5/16809 604/67 |
| 2015/0290387 A1 | 10/2015 | Vollstam | |
| 2017/0209639 A1 | 7/2017 | Wolter | |
| 2017/0348137 A1 | 12/2017 | Niels et al. | |

* cited by examiner

*Primary Examiner* — Joel M Attey
*Assistant Examiner* — Anna E Goldberg-Richmeier
(74) *Attorney, Agent, or Firm* — Kaplan Breyer Schwarz LLP

(57) ABSTRACT

Subject matter of the invention is a method for determining the difference in height level between a medical fluid pump and the body cavity of a patient for the correction of the measurement of the fluid pressure existing at the outlet end.

9 Claims, 4 Drawing Sheets

METHOD FOR ASCERTAINING THE VERTICAL DISTANCE BETWEEN A PATIENT (LEVEL OF SURGICAL INTERVENTION) AND A FLUID DELIVERY PUMP

SUBJECT MATTER OF THE INVENTION

The invention relates to a method for determining the difference in height level between a medical fluid pump and the body cavity of a patient for the correction of the fluid pressure acting at the outlet end.

PRIOR ART

It is known, in the field of the minimally invasive surgery (MIS), to pump fluids (e.g., aqueous rinsing solutions) into body cavities in order to expand the body cavity. For this purpose, the pressure must be sufficiently large in order to expand the tissue, however, must not become too large so not to damage the tissue. The measurement of the pressure in the body cavity is, thus, of high importance. For different reasons (e.g., space requirement and risk of contamination), there is no pressure sensor in the body cavity. Therefore, the result of the pressure measurement in the pump has to be used. The pressure measured in the pump is, however, only then identical to the pressure in the body cavity, when the pressure sensor of the pump is at the same height as the body cavity. When there is a difference in height level between the pressure sensor and the body cavity, then the value measured by the pressure sensor differs from the actual pressure value in the body cavity, with the difference being proportional to the difference in height. This potential difference in measurement due to the positioning of the pump relative to the patient is left out of consideration for pumps of prior art. There is, therefore, a need of a method, which determines the difference in height level between pump and body cavity of the patient before starting the surgery and corrects the measured pressure values, if needed.

The document US 2015/0290387A1 discloses a device for insufflation with a blood pressure-dependent pressure control. The document US 2008/0243054 A1 discloses a device for rinsing a body cavity, wherein the pressure and the flow of the rinsing liquid is regulated in dependence on the pressure in the rinsed body cavity. A determination of the difference in height level between pump and body cavity of the patient before starting the surgery is not mentioned in any of those documents.

As conditions for the application of the method according to the invention for the height detection that is intended for a certain situation in the field of medical treatment, does, however, not represent per se a treatment method of the human body, side conditions have to be met that are described in the following. The situation, in which the method according to the invention is employed, is as follows: At a fluid feed pump (5) (in the following referred to as pump), a desired target pressure is predetermined, which is to be applied, for instance, by means of a fluid for the expansion in a cavity of a patient (10). Such a cavity may be a natural cavity such as, e.g., a joint space or the abdomen or an artificially produced body cavity that is expanded for diagnostic and/or therapeutic purposes. The expansion occurs with a predetermined target pressure that is achieved and maintained by feeding the fluid into the cavity. For feeding such a fluid from a reservoir (1) into the cavity, according to the invention, a peristaltic pump is used as the pump (5).

As a measuring device for the pressure measurement, there is provided at least one pressure sensor (6) at the pump (5), which determines the feed pressure $P_{drv}$. In the case that the outlet end of the fluid line (7) or the surgery area (with the same meaning as the cavity expanded by fluid) is not at the same height level as the pump (5), the hydrostatic pressure ($P_{hyd}$) of the fluid in the tube section (7) will change the cavity pressure $P_{cav}$ or act on the value $P_{drv}$ measured by the pressure sensor. The value of the pressure sensor cannot be used, thus, without further compensation for the regulation of the cavity pressure $P_{cav}$. The cavity pressure $P_{cav}$ is the target quantity to be regulated and is to be held at a predetermined target pressure.

The starting situation, in which the method according to the invention is to be employed, can take place in various scenarios, regarding the difference in height level between feeding device and outlet end and regarding the situation at the outlet end. It is assumed that the scenarios in relation to the heights will not change over the time of application, i.e., from the first application of the method according to the invention, until the fluid connection to the reservoir is discarded and a new tube (3, 7) is brought into the fluid feed pump (5).

The object of the solution according to the invention is the determination of the patient's height level $h_{pat}$ (patient (10) may be positioned at a higher or lower level than the pump (5)), whereby the target value controlled by using the pressure sensor (6) can be compensated according to the actual conditions. Without this compensation, the pressure $P_{cav}$ in the cavity of the patient (10) cannot correctly be regulated to the target value.

In the case that the patient (10) is positioned at a higher level than the pump (5) (FIG. 1), the hydrostatic pressure ($P_{hyd}$) of the fluid in the tube section (7) has an effect on the sensor (6) as an offset fault and can be deducted according to prior art. According to the invention, an alternative solution for the pressure or height detection is described. The pressure in the water column can be transferred into the difference in height level to be determined in cm.

In the case that the patient (10) is positioned at a lower level than the pump (5) (FIG. 3), the hydrostatic pressure ($P_{hyd}$) of the fluid in the tube section (7) has an effect on the sensor (6) as an offset to the cavity pressure $P_{cav}$ in the patient (10). This case may also be detected with a pressure sensor (6), as long as this pressure sensor (6) can determine negative pressure values in relation to ambient pressure. When a pressure sensor (6) is used that can determine positive pressure values only, the above case cannot directly be determined by measurement. According to the invention, an alternative solution is described for the pressure or height detection.

In fluid feed pumps of prior art, a height difference correction is offered by predetermination/input of a value ($h_{pat}$) in the system settings of the fluid feed pump (5). In this height setting, according to prior art, only positive heights can be entered. This covers the case only that the surgery area/patient (10) is at a higher level than the pump (5). Based on this value, the hydrostatic pressure ($P_{hyd}$) at the sensor (6) is compensated (offset compensation), i.e., deducted from the measured value $P_{drv}$. This method is also described in the patent applications WO 2005/089832 A2 and WO 2005/042065 A2.

A method, which determines, based on one or several measurements, a patient's height level $h_{pat}$ is not known up to now.

SOLUTION ACCORDING TO THE INVENTION

Since, in the context of using the devices, a certain behavior can be imposed on the user, however, this cannot be verified by the manufacturer, and the manufacturer is responsible for the safe application, a technical method according to the invention being effective for all imaginable scenarios is embodied. First, the variants of the scenarios are described:

In principle, the position of the patient (10)—this means the body cavity to be expanded—above or below the transport roller wheel (4) has to be differentiated.

As an additional case, it has to be determined, whether the connection from the sensor (6) via the tube section (7), the connector with outlet valve (8) and an instrument (9) is open to the ambient atmosphere. In the case that the instrument (9) was introduced into a closed cavity of the patient (10), the hydraulic pressure ($P_{hyd}$) must be differentiated from the pressure in the cavity $P_{cav}$.

For the determination of the hydraulic pressure or the patient's height ($h_{pat}$), a method according to the invention based on the measurement of pressure values can be used.

For this purpose, it has to be verified, first, how many pressure sensors of which kind are provided in the pump. Normally, a pressure sensor is provided in the feeding direction behind the pump. This pressure sensor can permit uni- or bidirectional measurements, i.e., indicate either positive pressure values only, or positive and negative ones. Some pump models comprise an additional pressure sensor between the reservoir (1) and the pump (5).

The solution according to the invention for the determination of the patient's height level $h_{pat}$ that causes a hydrostatic pressure ($P_{hyd}$), has to differentiate between two applications:

I) The patient (surgery area) (10) is at a higher level than the pressure sensor (6) of the pump (5) ($h_{pat}>0$) as shown in FIGS. 1 and 2.

II) The patient (surgery area) (10) is at a lower level than the pressure sensor (6) of the pump (5) ($h_{pat}<0$) as shown in FIG. 3.

It is assumed, herein, that between the pressure sensor (6) and the hydraulically effective height of the transport roller wheel (4), there is no relevant difference in height. A value for 'no relevant difference in height' is ≤3 cm water column.

Further, there are different cases of the procedure:
a) An employed instrument (9) is outside of the patient (10) or the cavity of the surgery area, and the outlet end is open to the ambient atmosphere or to ambient pressure.
b) The employed instrument (9) was already introduced into the cavity of the surgery area, and a (increased and unknown) cavity pressure $P_{cav}$ acts at the outlet end.
c) The outlet valve (8) provided in the fluid connection is closed, or the tube section (7) is disconnected.

For the solution of this problem, the present patent application teaches the variants of the methods according to the independent claims 1 to 4. Further improvements according to the invention are taught by the dependent claims 5 to 7.

A central element of the present invention is the determination of the pressure in the tube systems by determination of the torque of the pump, with the torque being determined by the measurement of the current.

Variant 1: The embodiment of the present invention is illustrated in FIG. 2: A reservoir (1) is connected via a tube connection (3) to a roller wheel pump (5) according to the invention. The feed pump is connected via the tube (7) to a medical instrument (9), which is introduced into the body cavity of a patient (10). The hydrostatic pressure of the water column in the body cavity (10) of the patient is to be determined. The pressure $P_{cav}$ is made up of the partial pressures of the water column $P_{wat}$ before the feed pump and the pressure of the water column $P_{hyd}$ after the feed pump. The pressure $P_{wat}$ depends on the height of the reservoir above the pump, the pressure portion $P_{hyd}$ depends on the height level of the patient $h_{pat}$ above or below the transport wheel of the pump (5). When the patient's height is below the transport wheel, then the pressures $P_{wat}$ and $P_{hyd}$ add up to the total pressure in the body cavity, $P_{cav}$. When the patient is above the plane of the transport wheel, then the pressure $P_{wat}$ is reduced by the pressure $P_{hyd}$. The determination of the patient's height level $h_{pat}$ is thus in principle possible by measurement of the pressures $P_{wat}$ and $P_{hyd}$.

In the simplest case (see FIG. 2), the pump comprises two pressure sensors, namely one pressure sensor (11) before the feed pump (5) and one pressure sensor (6) after the feed pump (5). When the pressure sensor (6) is a bidirectional pressure sensor, then both pressures of the pressure sensors (11) and (6) can directly be read. From these pressure values, the patient's height can immediately be determined.

In this case, it is only needed to verify, whether the transport tube (7) with the medical instrument (9) is introduced into the body cavity, and whether the valve (8) is open. The partial process of the detection, whether the medical instrument is introduced into the body cavity, and whether the valve is open, can be performed as follows:

Crucial for the detection is the knowledge of the volume of the tubes of the transport tube (7). According to the invention, it is proposed to determine this volume before setting the pump into operation and to store it in the pump. In a normal clinical case, identical tube sets are always used, such that the volume of the tube needs to be determined once only. In a preferred embodiment of the invention, the volume of the tube is stored in a memory that is attached at the tube set, e.g., an RFID transponder. When placing the tube sets in the pump, the RFID transponder is read out, and the volume of the tube is made available to the pump. Alternatively, the transmission may also occur through other electrical/electronic, magnetic, or optical (e.g., barcode) transmission elements.

After storage of the volume of the tubes in a memory of the pump, feeding can be started. By indication of a pressure value of the pressure sensor (6) different from zero, the pump receives information that filling of the transport tube (7) is started. Since the fed amount of liquid is proportional to the turns of the pump, the liquid volume fed into the transport tube (7) can precisely be determined.

In the desired case that the medical instrument has already been fitted into the body cavity, and the valve (8) is open. In practice, the pressure oscillates, due to the peristaltics of the pump, slightly about a constant value (e.g., ±3 cm water column). Such slight oscillation about a constant value is considered constant, for the purposes described here. As soon as the liquid reaches the body cavity, as a consequence of the desired expansion of the body cavity, a higher pressure slowly builds up. The hydrostatic pressure $P_{hyd}$ searched for is, in this case, the pressure that is measured, after the fed volume corresponds to the volume of the tube.

In the case that the valve is closed, the feed pump (5) is not capable to fill up the complete tube, since the air present in the tube cannot escape and thus is compressed. This condition of the system is shown by that already prior to feeding a liquid volume, which corresponds to the volume of the tube, a significant pressure increase will happen. In this case, a measurement of the patient's height is not possible. The pump delivers in this case an alarm signal. When the valve is opened, the situation corresponds to the case described above.

In the case that the end of the transport tube or of the medical instrument should not be in the body cavity of the patient, then the pressure measured by the pressure sensor (6) is dependent on at which height the tube end is arranged. The pressure sensor indicates, after feeding a liquid volume, which corresponds to the volume of the tube, a pressure that will not increase with further feeding. In this case, too, an alarm signal of the pump is effected. After connection of the transport tube to a medical instrument or after introduction of the medical instrument into the body cavity of the patient, again the situation mentioned above is obtained that can be measured same as above.

Variant 2: In the case of a pump that comprises only one single pressure sensor (6) after the transport wheel (see FIG. 1), the process described above is to be modified as follows:

For determination of the pressure $P_{wat}$, with connected reservoir, first liquid is fed, until the pressure sensor (6) detects a pressure. This pressure indication serves as a hint that the tube is filled at least up to the position of the pressure sensor (6). At this point of time, feeding is stopped, the transport wheel (4) comes to standstill. Then, a "backward feeding" is initiated, e.g., the roller wheel turns in the opposite direction. In this backward feeding, the torque of the motor is determined. For this purpose serve current sensors (12) that measure the current flow during the backward feeding. The current flow is proportional to the torque. The torque is composed of a constant and a variable portion. This constant is formed by the rolling resistance of the pump (5) in combination with the material properties of the tube (3, 7). With constant tube materials, as they are used in the clinical environment, constancy can be assumed here. The second component of the torque is the hydrostatic pressure $P_{wat}$, against which the pump (5) has to operate. With known pumps and tube materials, therefore, the pressure $P_{wat}$ can be determined by measurement of the current flow by means of the current sensors (12).

After this determination of the pressure portion $P_{wat}$, the method can be performed as described above (Variant 1), in case that the pressure sensor (6) is a bidirectional pressure sensor as described above.

Variant 3: In the case that the pressure sensor (6) is a unidirectional pressure sensor that can measure, thus, only positive pressures, but not negative ones, the methods described above have to be modified as follows:

First, the pressure $P_{wat}$ is determined same as in Variant 1 or Variant 2. Then, by action of the roller wheel (4), a liquid volume is fed, which corresponds to the volume of the tube. As described in Variant 1, it is determined, whether the medical instrument is in the body cavity, and whether the valve (8) is open. When the valve (8) is open, and the medical instrument (9) is in the body cavity (10), a volume is fed, which corresponds to the volume of the tube, and the pressure sensor detects a positive pressure value, then this pressure value corresponds to the pressure $P_{hyd}$. The body cavity, thus, is positioned above the transport wheel, and from the measured pressure, the patient's height above the transport wheel can immediately be determined. When, however, the pressure sensor (6) indicates no pressure (pressure zero), then the patient is positioned either exactly on the height of the feed pump or below that. In this case, the pressure value $P_{hyd}$ can be determined as follows:

After feeding a liquid volume, which corresponds to the volume of the tube, the feed pump is stopped, and a "backward feeding" occurs by backward rotation of the transport wheel. In an analogous manner as in Variant 2 described above, the current flow is measured by means of the current sensors (12). The current flow, in turn, is proportional to the torque (with the addition of the constant described above), which is proportional to the total pressure. In this case, the torque indicates the pressure of the total liquid column, e.g., $P_{wat}+P_{hyd}$. By subtraction of the already known pressure $P_{wat}$ from the total pressure, the pressure $P_{hyd}$ can be determined, which again indicates the height of the body cavity of the patient below the feed pump.

The special advantage of the method according to the invention is that the data required for the precise measurement of the patient's height can quickly and precisely be determined. In a simple way, it can be determined, whether the transport wheel of the pump is at the same height as the body cavity of the patient, or whether significant deviations from the desired position exist. At the same time, alarms are given, if there are faulty operations (e.g., valve closed or tube not connected to the medical instrument).

DETAILED DESCRIPTION OF THE INVENTION

The solution according to the invention for the determination of the patient's height level $h_{pat}$ that causes a hydrostatic pressure ($P_{hyd}$), must differentiate between two cases:

I) The patient (surgery area) (10) is at a higher level than the pressure sensor (6) of the pump (5) ($h_{pat}>0$) (FIGS. 1 and 2).

II) The patient (surgery area) (10) is at a lower level than the pressure sensor (6) of the pump (5) ($h_{pat}<0$) (FIG. 3).

It is assumed, herein, that between the pressure sensor (6) and the hydraulically effective height of the transport roller wheel (4), there is no relevant difference in height. A value for 'no relevant difference in height' is ≤3 cm water column.

Further, there are different cases of the procedure:

a) An employed instrument (9) is outside of the patient (10) or the cavity of the surgery area, and the outlet end is open to the ambient atmosphere or to ambient pressure.

b) The employed instrument (9) has already been introduced into the cavity of the surgery area, and there acts a (higher and unknown) cavity pressure $P_{cav}$ at the outlet end.

c) The outlet valve (8) in the fluid connection is closed, or the tube section (7) is disconnected.

In the case I), a), a fluid of the pump (5) is fed from the reservoir (1), in order to fill the tube (3, 7) and the instrument (9) with the fluid. The pressure at the sensor (6) reaches a stationary value, i.e., it changes in its mean value in the lower single-figure percentage range only, when the tube (3, 7) and the instrument (9) are filled up. In this case, the pump (5) is stopped. The stationary pressure value ($P_{drv}$) measured after the stop of the pump (5) corresponds to the hydrostatic pressure ($P_{hyd}$). By the static deduction of the value $P_{hyd}$ from the sensor value $P_{drv}$, the hydrostatic pressure ($P_{hyd}$) is thus compensated.

In the case II), a), a fluid of the pump (5) is fed from the reservoir (1), in order to fill the tube (3, 7) and the instrument (9). The pressure at the sensor (6) reaches a stationary value, when the tube (3, 7) and the instrument (9) are filled up. In this case, the pump (5) is stopped. The measured stationary pressure value ($P_{drv}$) corresponds to the hydrostatic pressure ($P_{hyd}$), when a bidirectional pressure sensor is used that can measure positive and negative pressures relative to ambient pressure. In this case, the static value $P_{hyd}$ can be added to the sensor value $P_{drv}$, in order to determine the hydrostatic pressure ($P_{hyd}$) in the cavity and to compensate the measurement error.

In order to determine, in the case II), a), the hydrostatic pressure ($P_{hyd}$) by means of a unidirectional sensor, the method has to be extended. A unidirectional sensor can only measure values above ambient pressure, that is, positive values. After the tube (3, 7) and the instrument (9) have been filled with a liquid, and the pressure sensor (6) determines a stationary measurement value, the pump (5) is stopped. Then, the pump (5) is operated in the opposite feeding direction, and draws in the fluid in the tube section (7). By means of torque measurement of the pump motor, the necessary force or, under consideration of the inner diameter of the tube, the draw-in pressure ($P_m$) at the pump (5) can be deducted. Herein is torque~force~pressure. The determination of the torque may be made by measurement of the motor current of the transport roller wheel (4) of the pump (5). When the necessary draw-in pressure is known, at which the fluid from the tube (3, 7) and instrument (9) is fed back, the hydrostatic pressure ($P_{hyd}$) can be calculated thereby. This requires the knowledge in advance, how high the hydrostatic pressure $P_{wat}$ from the reservoir (1) to the pump level is. The calculation is made as per:

$$P_m - P_{wat} = P_{hyd}.$$

When the hydrostatic pressure $P_{wat}$ of the reservoir (1) is to be measured, there are two possibilities: First, the use of a second pressure sensor (11) between the transport roller wheel (4) and the reservoir (1). Second, a determination by measurement of the pressure $P_{wat}$ via the torque measurement of the fluid feed pump (5). In the second case, an initial measurement process is needed, before the hydrostatic pressure ($P_{hyd}$) in the tube section (7) and the instrument (9) can be determined. The pump (5) is started with no fluid in the tubes, in order to feed the fluid from the reservoir (1) into the tube section (3). At that moment, when the fluid reaches the transport roller wheel (4) or the location of the pressure sensor (6), and water is fed into the tube section (7) between pump (5) and patient (10), a pressure increase is detected at the pressure sensor (6). The pump (5) is stopped, and the feeding direction is changed (pump (5) feeds the fluid back to the reservoir (1), in the tube section (7) between pump (5) and patient (10) there is no significant amount of fluid). The necessary motor torque of the pump (5), in order to feed the fluid from the tube section (7) into the tube section (3) between reservoir (1) and pump (5), is proportional to the pressure $P_{wat}$, and the coefficient of proportionality can be determined previously by measurement for the employed inner diameter of the tube section (3). The procedure in this regard would be a previous measurement of the correlations and when putting the pump (5) into operation, an assignment of the coefficient of proportionality depending on the detected tube set. The detection and transmission of data may take place, e.g., by means of an RFID chip in the tube set.

In an alternative embodiment, from the inner diameter of the tube or the area of the tube cross-section in the tube section (3) calculated therefrom and motor torque, the pressure $P_{wat}$ and thus the height level between the transport roller wheel (4) and the fluid level in the reservoir (1) can mathematically be determined:

$$P_{wat} = (\text{motor torque})/(\text{radius of the transport roller wheel (4)} \cdot \text{area of the tube cross-section in the tube section (3)})$$

In the case I) b) and the case II) b), the methods from case I) a) and case II) a) can be used in a modified manner. First, the tube section (7) between pump (5) and patient (10) and the instrument (9) is filled via the pump (5) with a fluid, until the pressure at the sensor (6) becomes stationary. When the instrument (9) is introduced into a closed cavity in the patient (10) (see FIG. 4, point of time $t_0$), the pressure will continue to increase and will not reach a stationary value, as long as the pump (5) feeds a fluid (FIG. 4, curve with flow (volume flow) q=constant). From this detected course of the pressure signal, it can be concluded that case I) b) and case II) b) are present. In this case, the pressure value at the sensor (6) at the point of time $t_0$ is assigned as hydrostatic pressure $P_{wat}$.

If a unidirectional pressure sensor should be employed, the pump must be stopped at the point of time to, and the method described above under case II), a) should be performed, in order to calculate the hydrostatic pressure $P_{wat}$.

In the case I) c) and the case II) c), at first, no values can be determined. Prior to the use of the device and thus prior to the necessity to use a height detection for the compensation, a situation according to the case a) will occur, since the user has confirmed that the tube is filled and correspondingly the height detection will be made. It is assumed that in normal use, the case b) cannot occur subsequently to a case c). If this does occur, nevertheless, the starting value at a pressure drop will be used as the difference in height level $h_{pat}$.

EMBODIMENTS

The method according to the invention for determining the difference in height level $h_{pat}$ between patient (10) and fluid feed pump (5) is as follows:

The initial situation is the provision of the fluid feed pump (5) comprising a reservoir (1) arranged thereabove, wherein the fluidic connection paths in the devices according to the application are provided, are, however, still unfilled. The pump device was turned on and is ready to work, the self test is completed.

In a first step, the fluid feed pump (5) feeds, through the through-going fluidic connection of the reservoir (1), the fluid and stops feeding, as soon as the pressure sensor (6) detects a change in pressure, which in this situation is caused by the fed water column. Thereby, by the measurement value of the pressure sensor, under the condition of an empty tube (3, 7), the situation can be detected that the fluid column extends from the reservoir (1) to the fluid feed pump (5) and the rest is filled with air.

The mentioned stop of feeding consists—if a pressure sensor (11) is attached hydraulically shortly before or above the transport roller wheel (4)—in that the value measured at this optional pressure sensor (11) is maintained for further processing, which not necessarily means a standstill of the transport roller b (4). If no other pressure sensor (6) than the one shown in FIGS. 1 to 3 is available, then the transport roller wheel (4) is turned backward. From a measurement of the motor current required for feeding from the tube section (3) to the reservoir (1) (also for the backward feeding), the generated torque is derived. The torque is calculated with the diameter of the transport roller wheel as a force and is calculated, together with the previously known effective area of the tube cross-section, as a pressure value (force/surface area), from which the height between the fluid level in the reservoir (1) and the hydraulically effective height of the transport roller wheel (4) is obtained.

Between the hydraulically effective height at the transport roller wheel (4) toward the reservoir (1) and the hydraulically effective height at the transport roller wheel (4) toward the patient (10), there is, if applicable, a difference that has to be determined beforehand.

After the pressure $P_{wat}$ or the height value between the fluid level in the reservoir (1) and the fluid feed pump (5) has been determined, the tube and instrument filling process is continued, i.e., the pump (5) continues to feed fluid in the direction of the patient (10). Feeding continues until the tube section (7) is completely filled. When the fluid exits from the open end of the tube section (7) or the instrument (9), which is detected by the cease of the pressure increase described above (embodiment) or by that the fed volume is larger than the volume of the tube of the tube section (7) between feeding segment and outlet end (alternative embodiment), the filling phase/feeding is terminated. This means in reality that the pump feeds from this point of time on with constant volume flow, whereupon a constant pressure value at the pressure sensor (6) is obtained, and the pressure value is evaluated in relation to the fed volume. In an alternative embodiment, the fed volume is evaluated, and the fed volume is determined from the turns of the transport roller wheel (4) and the previously known feeding volume per turn. The fluid feed pump (5) is stopped, and the pressure value of the pressure sensor (6) is evaluated. When the pressure value is positive, this pressure value is used to determine the height level between the transport roller wheel (4) and the patient (10), and thereby it is assumed that in this case, the pump (5) is below the height level of the patient (10).

When the pressure value is negative, the measured pressure value is used as $P_{hyd}$, or therefrom the difference in height level $h_{pat}$ is determined, and thereby it is assumed that in this case, the pump (5) is above the height level of the patient (10).

When the pressure value is 0 (zero), it is assumed that in this case, the pressure sensor (6) cannot measure negative values, and that the pump (5) is above the height level of the patient (10). When this is the case, the transport roller wheel (4) is turned backward, and the motor current required for feeding from the tube section (7) to the reservoir (1) (i.e., for backward feeding) is measured, and therefrom the generated torque is derived. The torque is calculated with the diameter of the transport roller b as a force and is calculated together with the previously known effective area of the tube cross-section as a pressure value (force/area), which yields the height level between the transport roller wheel (4) and the height level of the patient (10).

When the pressure value, after a predetermined time, does not become a stationary value, it is assumed that in this case, the outlet end is placed in the cavity. The predetermined time follows from the tube filling time given by the feeding rate and the cross-sectional area of the tube plus optionally a small addition for rinsing-out of air bubbles. In the case that the outlet end is already in the cavity, then according to the invention, the pressure increase is to be evaluated, in order to determine the patient's height level $h_{pat}$. The evaluation consists in detecting the course as exemplarily shown in FIG. 4, and using the value at the point of time $t_0$ as the hydrostatic pressure $P_{wat}$ or, derived therefrom, to determine the difference in height level $h_{pat}$ between pump (5) and patient (10). It is necessary, herein, that a constant volume flow of the fluid is generated.

According to the invention is also provided a test, as to whether there is an open end of the tube section (7) or instrument (9), since a connector with an outlet valve (8) is provided that may be closed, and clamps may be attached at the tube. This method considers the pressure values together with the fed fluid volume. When a volume flow is fed, and the pressure moves toward a constant value at the pressure sensor (6), it is assumed that in this case, the tube section (7) is open to ambient pressure. When feeding is stopped, the pressure will decrease, and the measurement value at the pressure sensor (6) decreases. When these measurement values occur in the flow and pressure course, it is assumed that in this case, the end of the tube section (7) is open to ambient pressure.

When the flow values are zero, and the pressure remains stable or decreases slightly only, it is assumed that in this case, the end of the tube section (7) is closed to ambient pressure. In the case that the tube filling process is just terminated, it is assumed that in this case, the outlet valve at the connector (8) is closed, or a clamp clamps the tube section (7) off. In this case, in the further course of the use of the pump (5), a user will verify the tube filling process, which means that the outlet valve of the connector (8) is shortly opened and closed, and some fluid will escape. The pressure sensor (6) detects the pressure drop by opening the outlet valve at the connector (8), whereupon, as intended, the feeding of the fluid feed pump (5) will start, in order to maintain the preset pressure. Since the fluid feed pump (5) has detected the situation, the pressure value of the hydrostatic pressure, as already described, is determined by the pressure sensor (6) or the backward feeding, and so to speak retrospectively, the pressure value at the start of feeding or with still closed valve (8) is taken as the value $P_{wat}$, or the patient's height level $h_{pat}$ is determined therefrom.

LIST OF REFERENCES

Outlet end refers to the transition of the fluid line after the transport roller wheel (4) to ambient pressure or to the cavity. This may be the end of the tube section (7) or the end of the outlet valve (8) or the end of the instrument (9), depending on where ambient pressure acts, when the method according to the invention is applied.

$h_{pat}$—patient's height level=hydraulically effective height level between the transport roller wheel (4) and the patient (10)

P—pressure $P_m$—draw-in pressure $P_{cav}$—cavity pressure $P_{drv}$—feed pressure $P_{hyd}$—hydrostatic pressure of the fluid in the tube $P_{wat}$—pressure of the water column before the feed pump Q—volume flow (1) reservoir of the fluid.

(2) spikes forming a connection between reservoir and tube (3). Usually, clamping devices may be provided here for a container exchange.

(3) tube section of the tube set between reservoir (1) or spikes (2) and transport roller wheel (4), also fluid line.

(4) transport roller wheel.

(5) fluid feed pump or pumping device or pump.

(6) pressure sensor-bidirectional design (measures also negative pressures in relation to ambient pressure) or unidirectional design (measures only pressure values above ambient pressure).

(7) tube section between fluid feed pump (5) and connection to a connector (8) or instrument (9), also fluid line.

(8) connector with outlet valve, optionally provided.

(9) instrument, which is introduced into the cavity to be expanded and from the end of which the fed fluid exits into the cavity. Frequently, a combination of sleeve (=trocar) and endoscope or shaver.

(10) patient=region of surgery=surgery area=cavity=body cavity.

(11) optional pressure sensor, hydraulically shortly above the transport roller wheel (4).
(12) current sensor at the motor that moves the transport roller wheel (4) of the fluid feed pump (5).

Figure 1:
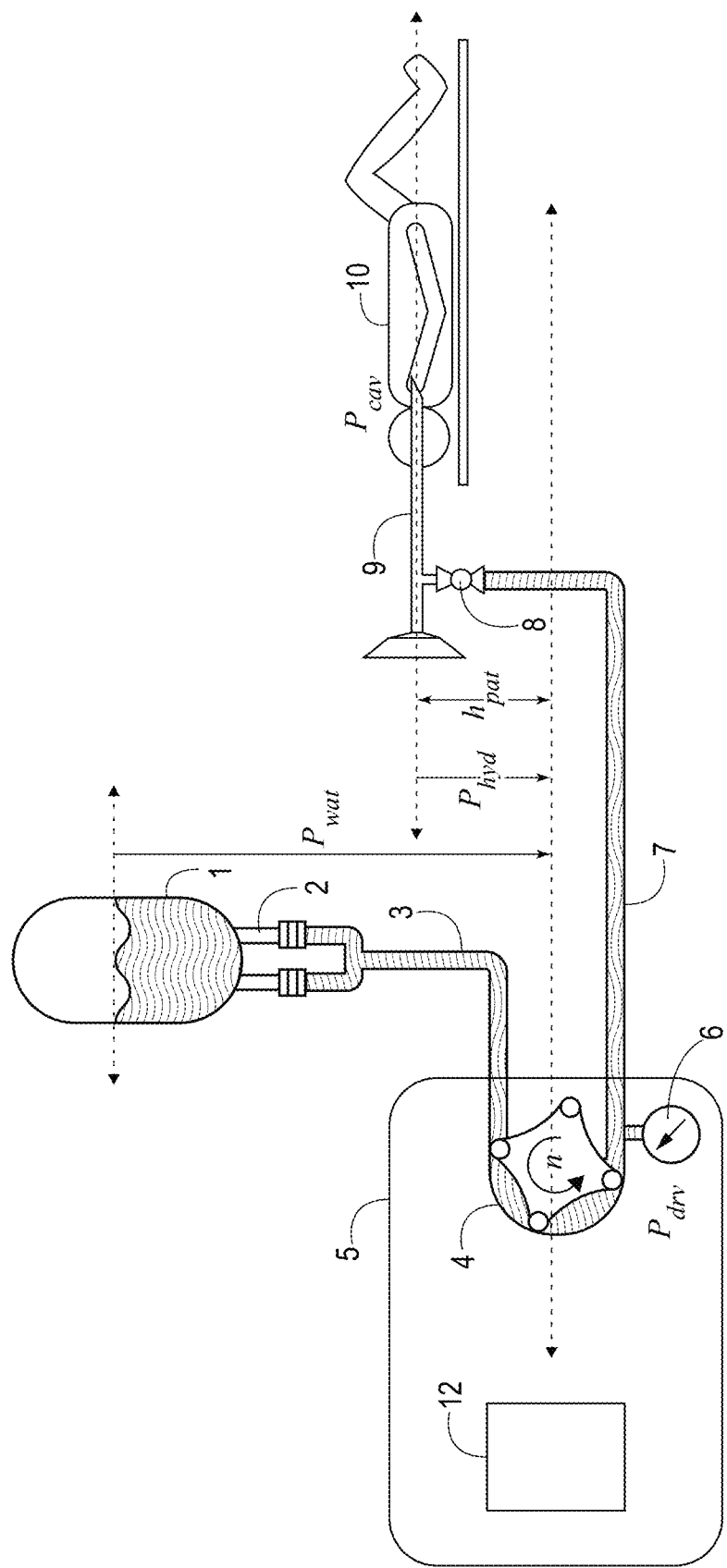
FIG. 1 shows a medical fluid pump and a body cavity in which the body cavity is located higher than the fluid pump. The difference in height is calculated using data from a single pressure sensor in the fluid line between the fluid pump and the body cavity.
Figure 2:
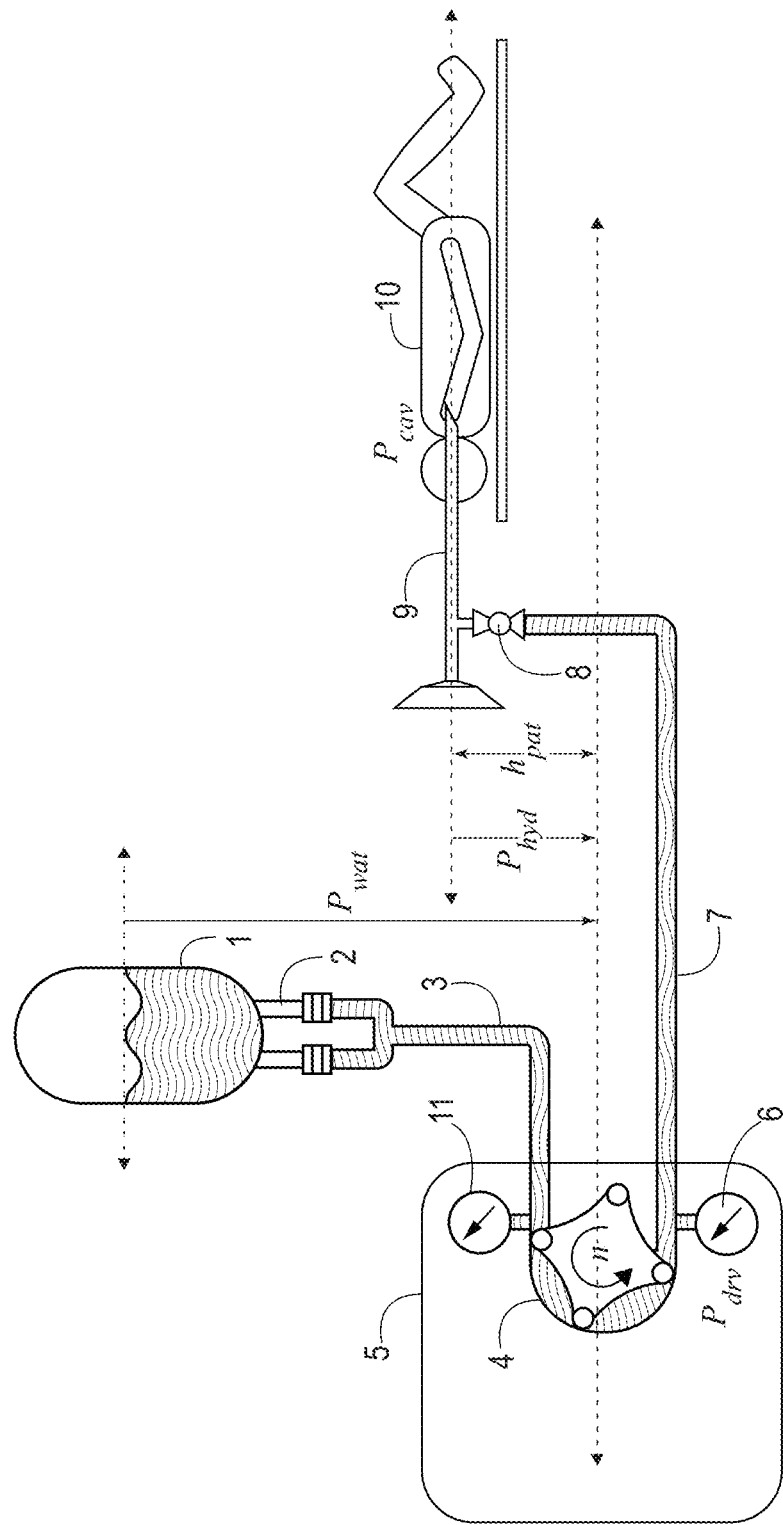
FIG. 2 shows a medical fluid pump and a body cavity in which the body cavity is located higher than the fluid pump. The difference in height is calculated using data from two pressure sensors.
Figure 3:
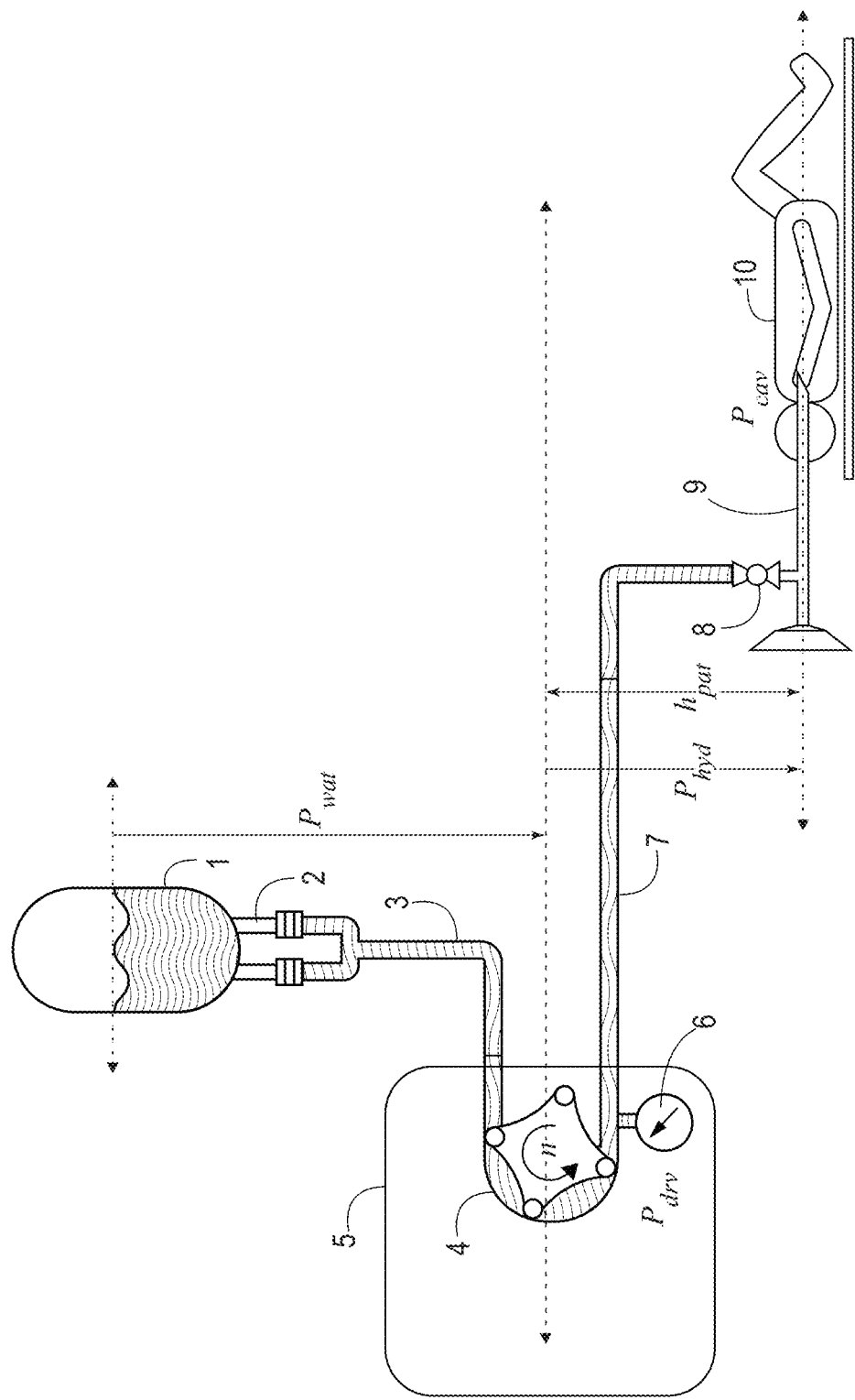
FIG. 3 shows a medical fluid pump and a body cavity in which the body cavity is located lower than the fluid pump. The difference in height is calculated using data from a single pressure sensor in the fluid line between the fluid pump and the body cavity.
Figure 4:
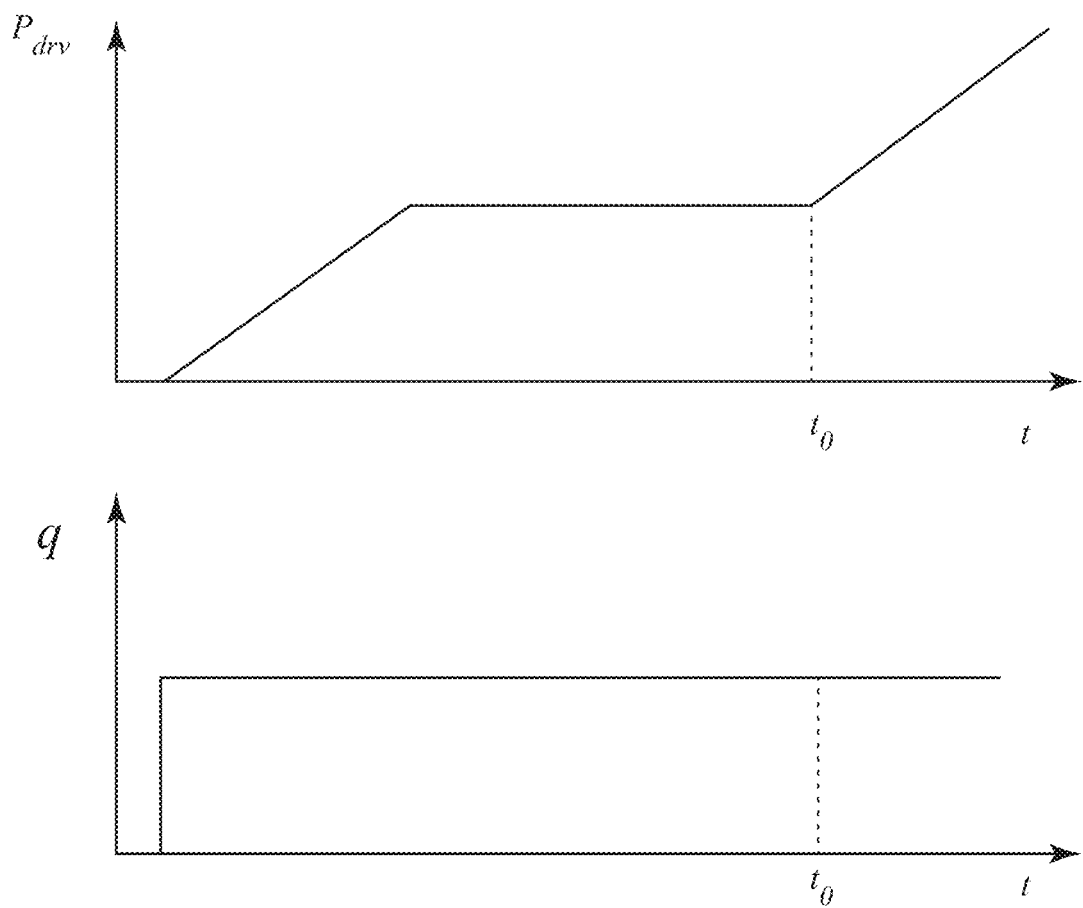
FIG. 4 shows the relationship between liquid feed with a pump and the pressure reading in a situation in which the outlet of the fluid line is located in a closed cavity of the patient.

The invention claimed is:

1. A method for determining a difference in height level $h_{pat}$ between a patient (10) and a fluid feed pump (5) with a current sensor (12) and with a bidirectional pressure sensor (6) in a second tube section (7) between fluid feed pump (5) and connection to a connector (8) or an instrument (9),
comprising a reservoir (1) of a medical device arranged above the fluid feed pump (5), fluidic connection paths that are initially unfilled, and a volume of the fluidic connection paths being known, characterized by the following steps:
a) fluid feeding by the fluid feed pump (5) with a transport roller wheel (4) through a through-going fluidic connection of the reservoir (1),
b) stop fluid feeding as soon as the bidirectional pressure sensor (6) detects a change in pressure, which is caused by a fed water column,
c) backward rotation of the transport roller wheel (4) while measuring, by the current sensor (12), a motor current required for feeding from a first tube section (3) to the reservoir (1),
d) calculation of a pressure value $P_{wat}$ of a water column before the fluid feed pump from the required motor current,
e) continuation of fluid feeding until the second tube section (7) is completely filled,
f) detection of the fluid exiting from an open end of the second tube section (7) or the instrument (9) by evaluation of the pressure values at the bidirectional pressure sensor (6),
g) termination of fluid feeding,
h) evaluation of a pressure value $P_{hyd}$ of the bidirectional pressure sensor (6),
i) use of the pressure value $P_{hyd}$ for the determination of the difference in height level $h_{pat}$ between the fluid feed pump and the patient (10),
wherein when the pressure value $P_{hyd}$ is positive, this indicates that the fluid feed pump (5) is below the height level of the patient (10),
when the pressure value $P_{hyd}$ is negative, this indicates that the fluid feed pump (5) is above the height level of the patient (10),
when the pressure value $P_{hyd}$ is 0 (zero), this indicates that the fluid feed pump (5) is at a height level of the patient (10).

2. The method according to claim 1, wherein the detection of a proper exit of the fluid through the second tube section (7) and the medical instrument (9) in a cavity of the patient (10) is performed by the following steps:
a) fluid feeding by the fluid feed pump (5), until a pressure value different from zero is indicated at the bidirectional pressure sensor (6),
b) further fluid feeding, until a fed volume is larger than a volume of the tube, with the pressure measured at the bidirectional pressure sensor (6) remaining constant,
c) detection of a pressure increase at the bidirectional pressure sensor (6) after feeding a liquid volume, which is larger than the volume of the tube.

3. The method according to claim 1, wherein detection of a faultily closed valve (8) is performed by the following steps:
a) fluid feeding by the fluid feed pump (5), until a pressure value different from zero is indicated at the bidirectional pressure sensor (6),
b) further fluid feeding, wherein the pressure measured at the bidirectional pressure sensor (6) increases, before a fed volume corresponds to a volume of the tube.

4. The method according to claim 1, wherein detection of the instrument faultily not being in a body cavity of the patient or of a non-closed connection between the second tube section (7) and the instrument (9) is performed by the following steps:
a) fluid feeding by the fluid feed pump (5), until a pressure value different from zero is indicated at the bidirectional pressure sensor (6)
b) further fluid feeding, until a fed volume is larger than a volume of the tube, with the pressure measured at the bidirectional pressure sensor (6) remaining constant,
c) detection that after feeding a liquid volume, which is larger than the volume of the tube, no pressure increase is measured at the bidirectional pressure sensor (6).

5. The method according to claim 1, wherein the volume of the fluidic connection paths of the fluid feed is read out from an information carrier provided at a tube set prior to starting the fluid feeding.

6. The method according to claim 5, characterized by that the information carrier is an RFID-Chip, a magnetic tape, a barcode or an EPROM.

7. A method for determining a difference in height level $h_{pat}$ between a patient (10) and a fluid feed pump (5) with a current sensor (12) and with a unidirectional pressure sensor (6) in a second tube section (7) between fluid feed pump (5) and connection to a connector (8) or an instrument (9),
comprising a reservoir (1) of a medical device arranged above the fluid feed pump (5), fluidic connection paths that are initially unfilled, and a volume of the fluidic connection paths being known, characterized by the following steps:
a) fluid feeding by the fluid feed pump (5) with a transport roller wheel (4) through a through-going fluidic connection of the reservoir (1),
b) stop fluid feeding as soon as the unidirectional pressure sensor (6) detects a change in pressure, which is caused by a fed water column,
c) backward rotation of the transport roller wheel (4) while measuring, by the current sensor (12), a motor current required for feeding from a first tube section (3) to the reservoir (1), d) calculation of a pressure value $P_{wat}$ of a water column before the fluid feed pump from the required motor current,
e) continuation of tube and instrument filling until the second tube section (7) is completely filled,
f) detection of the fluid exiting from an open end of the second tube section (7) or instrument (9) by evaluation of pressure values at the unidirectional pressure sensor (6),
g) termination of fluid feeding,
h) evaluation of a pressure value $P_{hyd}$ of the unidirectional pressure sensor (6),
i) use of a positive pressure value $P_{hyd}$ for the determination of the difference in height level $h_{pat}$ between the fluid feed pump and the patient (10),
wherein when the pressure value $P_{hyd}$ is positive, this indicates that the fluid feed pump (5) is below the height level of the patient (10),
when the pressure value $P_{hyd}$ is 0 (zero), this indicates that the fluid feed pump (5) is at the height level of the patient (10) or above the height level of the patient (10),
j) in case of a pressure value $P_{hyd}$ being 0 (zero), backward feeding of the fluid by backward rotation of the transport roller wheel (4),
k) determination of a motor current by evaluation of the current sensor (12) and calculation of the pressure for the determination of the difference in height level $h_{pat}$ between the patient (10) and the fluid feed pump (5).

8. A method for determining a difference in height level $h_{pat}$ between a patient (10) and a fluid feed pump (5) with a current sensor (12) and with a bidirectional pressure sensor (6) in a second tube section (7) between fluid feed pump (5) and connection to a connector (8) or instrument (9), and with a second pressure sensor (11) between a reservoir (1) and a transport roller wheel (4) with the reservoir (1) of a medical device being arranged above the fluid feed pump (5), wherein fluidic connection paths that are initially unfilled, and a volume of the fluidic connection paths being known, characterized by the following steps:
   a) fluid feeding by the fluid feed pump (5) with a transport roller wheel (4) through a through-going fluidic connection of the reservoir (1) to the transport roller wheel,
   b) stop fluid feeding as soon as the bidirectional pressure sensor (6) detects a change in pressure, which is caused by a fed water column,
   c) reading a pressure value $P_{wat}$ at the second pressure sensor (11),
   d) continuation of tube and instrument filling until the second tube section (7) is completely filled,
   e) detection of the fluid exiting from an open end of the second tube section (7) or instrument (9) by evaluation of the pressure values at the bidirectional pressure sensor (6)
   f) termination of fluid feeding,
   g) evaluation of a pressure value $P_{hyd}$ of the bidirectional pressure sensor (6),
   h) use of the pressure value $P_{hyd}$ for the determination of the difference in height level $h_{pat}$ between the fluid feed pump and the patient (10),
   wherein when the pressure value $P_{hyd}$ is positive, this indicates that the fluid feed pump (5) is below the height level of the patient (10),
   when the pressure value $P_{hyd}$ is negative, this indicates that the fluid feed pump (5) is above the height level of the patient (10),
   when the pressure value $P_{hyd}$ is 0 (zero), this indicates that the fluid feed pump (5) is at the height level of the patient (10).

9. A method for the determination of a difference in height level $h_{pat}$ between a patient (10) and a fluid feed pump (5) with a current sensor (12) and with a unidirectional pressure sensor (6) in a second tube section (7) between fluid feed pump (5) and connection to a connector (8) or instrument (9), and with a second pressure sensor (11) between a reservoir (1) and a transport roller wheel (4), with the reservoir (1) of a medical device being arranged above the fluid feed pump (5), fluidic connection paths that are initially unfilled, and a volume of the fluidic connection paths being known, characterized by the following steps:
   a) fluid feeding by the fluid feed pump (5) with a transport roller wheel (4) through a through-going fluidic connection of the reservoir (1)
   b) stop fluid feeding as soon as the unidirectional pressure sensor (6) detects a change in pressure, which is caused by a fed water column,
   c) reading a pressure value $P_{wat}$ at the second pressure sensor (11),
   d) continuation of tube and instrument filling until the second tube section (7) is completely filled,
   e) detection of the fluid exiting from an open end of the second tube section (7) or instrument (9) by evaluation of the pressure values at the unidirectional pressure sensor (6),
   f) termination of fluid feeding,
   g) evaluation of a pressure value $P_{hyd}$ of the unidirectional pressure sensor (6),
   h) use of a positive pressure value $P_{hyd}$ for the determination of the difference in height level $h_{pat}$ between the fluid feed pump and the patient (10),
   wherein when the pressure value $P_{hyd}$ is positive, this indicates that the fluid feed pump (5) is below the height level of the patient (10),
   when the pressure value $P_{hyd}$ is 0 (zero), this indicates that the fluid feed pump (5) is at the height level of the patient (10) or above the height level of the patient (10),
   i) in a case of a pressure value $P_{hyd}$ 0 being (zero), backward feeding of the fluid by backward rotation of the transport roller wheel (4),
   j) determination of a motor current by evaluation of the current sensor (12) and calculation of the pressure for the determination of the difference in height level $h_{pat}$ between the patient (10) and the fluid feed pump (5).

* * * * *